United States Patent
Vason et al.

[11] Patent Number: 5,431,878
[45] Date of Patent: Jul. 11, 1995

[54] REFUSE STERILIZATION SYSTEM

[75] Inventors: James H. Vason; Donald Tuel, both of Hapeville, Ga.

[73] Assignee: Atlanta International Waste, Inc., Hapeville, Ga.

[21] Appl. No.: 191,220

[22] Filed: Feb. 4, 1994

Related U.S. Application Data

[62] Division of Ser. No. 967,402, Oct. 28, 1992, abandoned.

[51] Int. Cl.6 .................................................. A61L 2/06
[52] U.S. Cl. ............................................ 422/26; 422/3; 422/25; 422/295; 422/307
[58] Field of Search ................... 422/25, 26, 3, 292, 422/295, 297, 900, 307, 309

[56] References Cited

U.S. PATENT DOCUMENTS

| | | |
|---|---|---|
| 4,316,871 | 2/1982 | De Fraites ......................... 422/26 |
| 5,149,507 | 9/1992 | Ellis, Jr. ........................... 422/295 |
| 5,217,688 | 6/1993 | Von Lersner ..................... 422/309 |
| 5,223,231 | 6/1993 | Drake ............................... 422/297 |
| 5,246,674 | 9/1993 | Katschnig et al. ................. 422/299 |
| 5,290,511 | 3/1994 | Newman ........................... 422/299 |

Primary Examiner—James C. Housel
Assistant Examiner—Rachel Freed
Attorney, Agent, or Firm—James B. Middleton

[57] ABSTRACT

Refuse is sterilized by a system in which refuse is placed into a dumpster, the dumpster having an injection manifold adjacent to the bottom. The dumpster is placed into an autoclave, and steam enters the autoclave and is directed through the injection manifold so that all the steam passes through the refuse. The pressure within the autoclave is controlled to remain relatively low, around 20 psi, and the steam is continued until the temperature is at least 212° F.

7 Claims, 2 Drawing Sheets

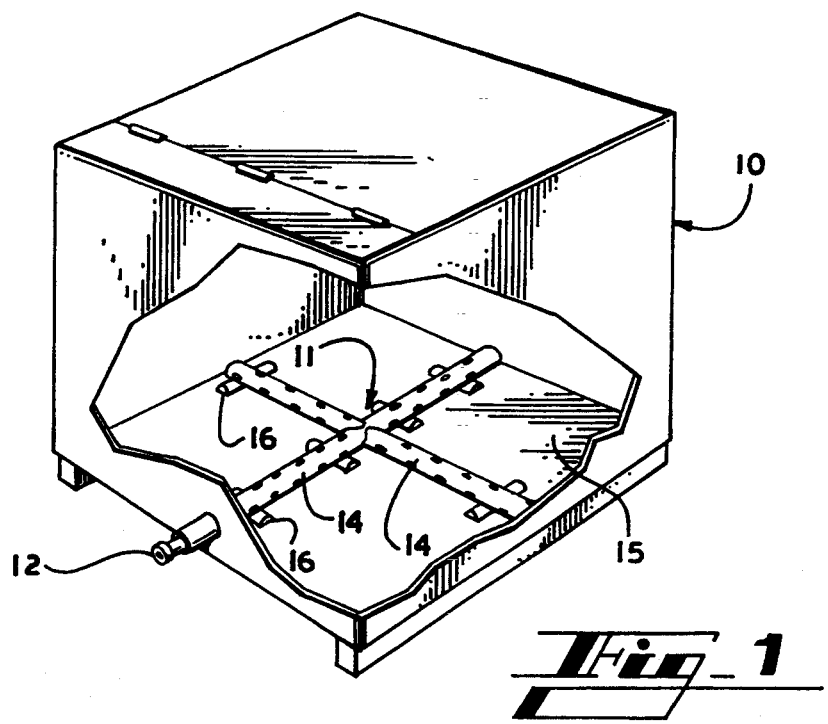
Fig_1
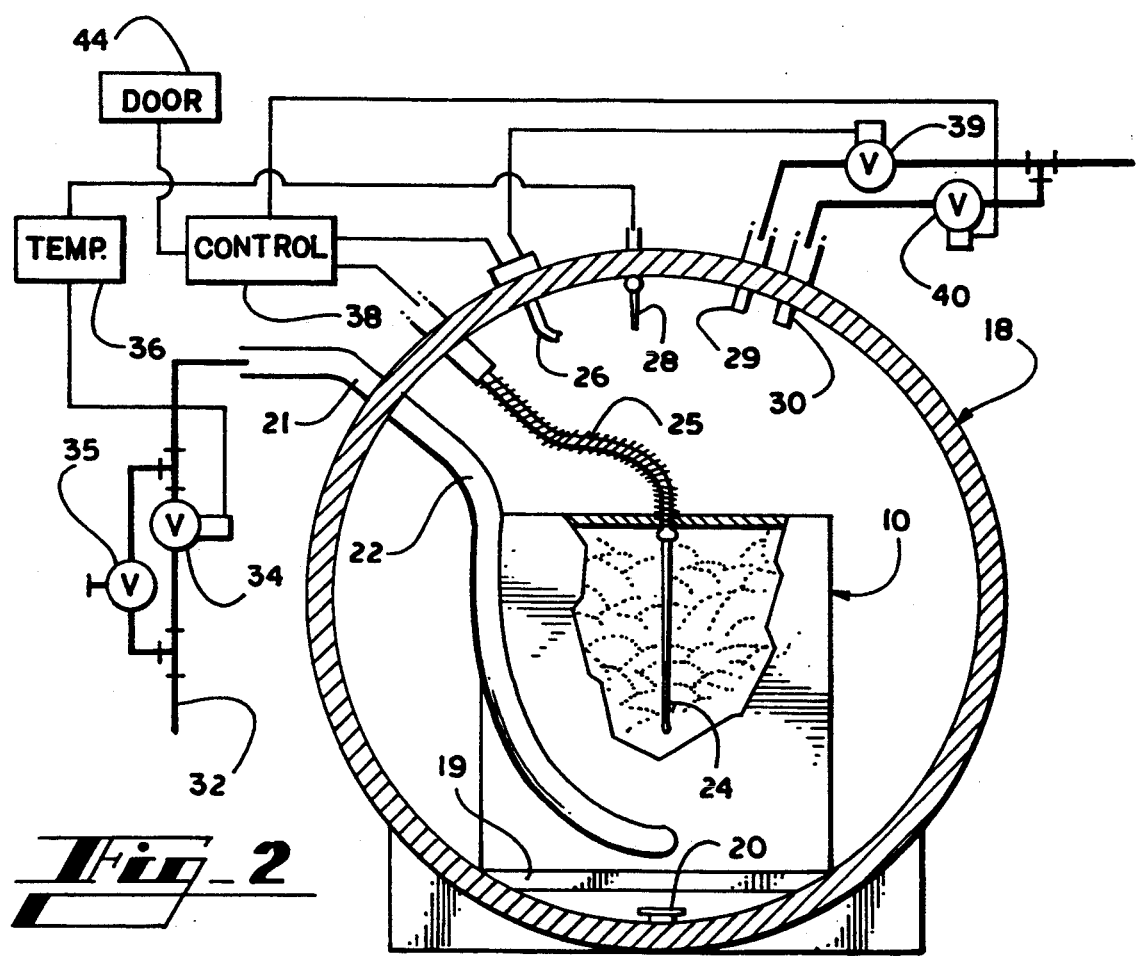
Fig_2

000000000000000000000# REFUSE STERILIZATION SYSTEM

CROSS-REFERENCE TO RELATED APPLICATION

This application is a division of the application by the same inventors, filed Oct. 28, 1992, under Ser. No. 07/967,402, titled "Refuse Sterilization System", now abandoned.

BACKGROUND OF THE INVENTION

Field of the Invention

This invention relates generally to refuse processing systems, and is more particularly concerned with a method and apparatus for sterilizing refuse.

Discussion of the Prior Art

There are several situations in which refuse must be sterilized before the refuse can be placed in the waste stream. Highly toxic materials, for example from hospitals and other health care institutions, is frequently incinerated to assure sanitary disposal. Less toxic materials, however, may be sterilized and placed into the normal waste stream. One example of the less toxic materials is the refuse from international airlines flights. In the United States, all refuse from international flights must be sterilized before the refuse can be placed in the waste stream.

It is well known that one can sterilize material through the use of an autoclave, wherein steam is used to heat the material to a predetermined temperature. The prior art includes an autoclave for refuse, the autoclave being of such size as to receive a standard size of refuse container. In using an autoclave, those skilled in the art will understand that the refuse is placed into the autoclave, and the autoclave is sealed. Steam is then admitted, and pressure within the autoclave increases so the temperature can be increased beyond the boiling point of water.

The minimum requirements for the sterilization of refuse from international flights include holding the refuse at a temperature of 212° F., or 100° C., for thirty minutes. If the location for the sterilization is above sea level, pressurization is required to reach the necessary temperature, so the autoclave is the obvious solution. It has been found, however, that the pressure exerted on the refuse compacts the refuse so that the center of the refuse does not become sufficiently heated. As a result, the necessary temperature may not be reached without raising the pressure, but the center of the refuse may not be heated when the pressure is raised to reach the necessary temperature. The prior art therefore does not provide a simple and efficient method for sterilizing refuse.

SUMMARY OF THE INVENTION

The present invention provides a system for sterilizing refuse wherein the refuse is within a container, and the container is received within an autoclave. Heated fluid is admitted into the refuse container so that the heated fluid passes through the refuse itself. The heated fluid passes from the refuse container and into the interior of the autoclave to pressurize the autoclave; however, the pressure within the autoclave is held to a relatively low pressure, and introduction of heated fluid is continued until the temperature of the autoclave reaches a predetermined temperature. The predetermined temperature is held for a predetermined length of time, and the pressure is released, the autoclave opened, and the refuse container removed.

In the preferred embodiment of the invention, the temperature within the refuse itself is monitored to assure proper sterilization.

BRIEF DESCRIPTION OF THE DRAWINGS

These and other features and advantages of the present invention will become apparent from consideration of the following specification when taken in conjunction with the accompanying drawings in which:

FIG. 1 is a perspective view showing a refuse container made in accordance with the present invention, partially broken away to illustrate the construction;

FIG. 2 is a cross-sectional view showing an autoclave with the refuse container of FIG. 1 therein, and showing the controls schematically; and, FIG. 3 is a flow chart illustrating the operating procedure for carrying out the method of the present invention.

DETAILED DESCRIPTION OF THE EMBODIMENT

Figure 3:
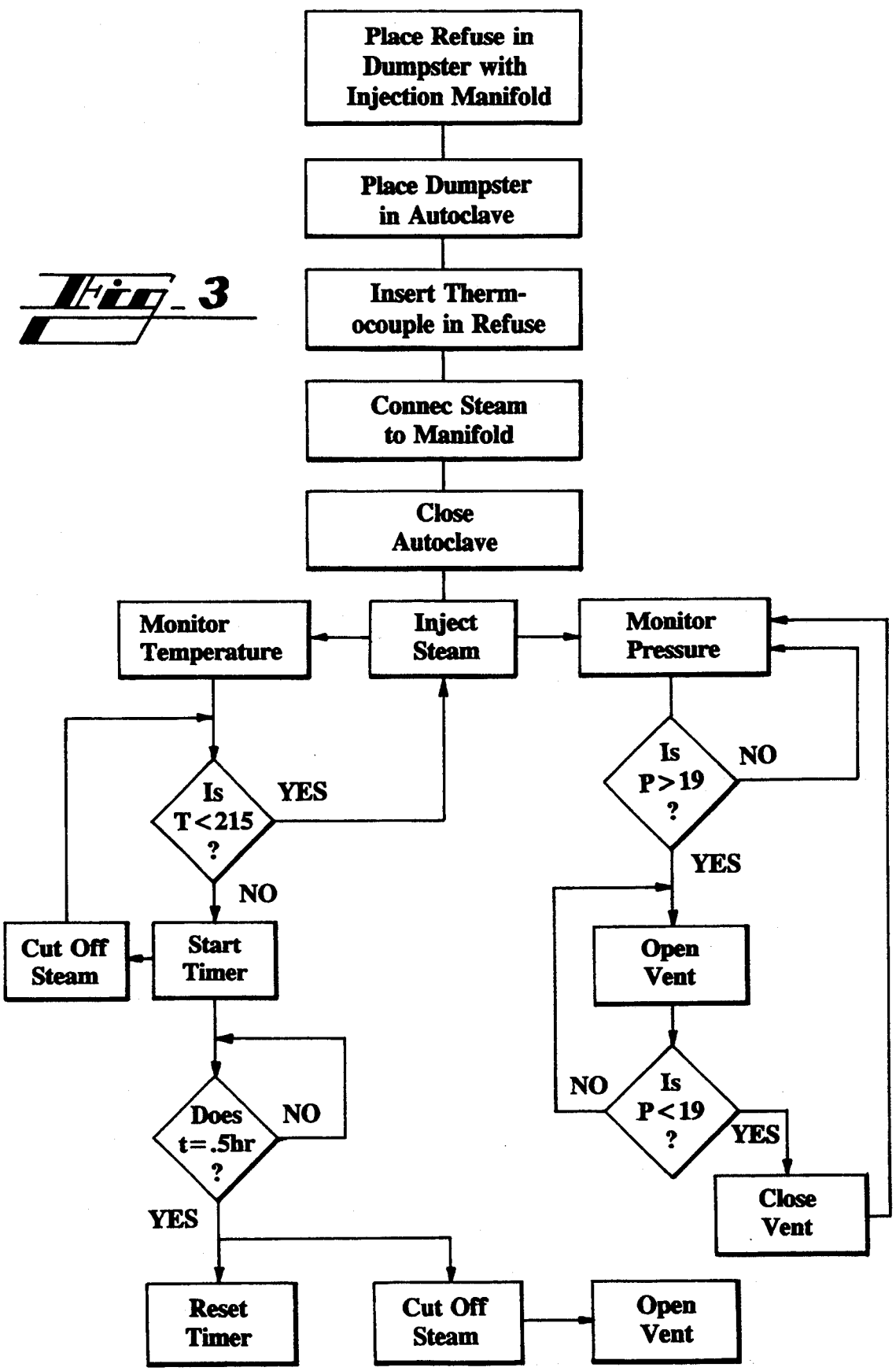

Referring now more particularly to the drawings, and to that embodiment of the invention here chosen by way of illustration, FIG. 1 shows a generally conventional refuse container generally designated at 10. The container 10 may be of the type referred to as a "dumpster", which is arranged to be emptied by handling mechanically. The details of the construction of the dumpster 10 are not here shown, but such dumpsters are well known to those skilled in the art. There are several designs of dumpsters and no particular design is required for use in the present invention.

The only modification to the conventional dumpster consists of the addition of the injection manifold generally designated at 11. The manifold 11 includes an external connector 12, preferably utilizing a quick disconnect, and perforated interior pipes 14. The pipes 14 are here shown in the form of a cross within the container 10. Those skilled in the art will understand that many different configurations may be used, the object being only to distribute the heated fluid in the container.

The manifold 11 is supported above the floor 15 of the container 10 by support blocks 16. The manifold 11 is preferably held about two inches, or about 5 cm, off the floor 15. This spacing allows the fluid to be injected into the refuse without unduly heating the floor 15 of the container 10.

An understanding of the overall invention will be had by referring to FIG. 2 of the drawings. FIG. 2 shows a conventional autoclave designated at 18. Those skilled in the art will understand that the autoclave 18 includes a large body provided with an end door (not shown) that can be opened, or can be closed to seal the interior. The construction of the autoclave 18 should therefore be understood without further description.

As shown in FIG. 2, the container 10 is within the autoclave 18. The autoclave 18 is provided with a platform 19 to receive the container 10, and the space below the platform 19 may have a drain 20 leading to the sanitary sewer line.

Whereas the conventional autoclave includes a steam inlet whereby the interior of the autoclave is directly pressurized by fluid under pressure, usually steam, the present arrangement includes a steam inlet 21 connected to a flexible hose 22. The hose 22 terminates in a coupling that is receivable on the connector 12 of the manifold 11. Thus, steam enters the autoclave 18, but passes through the flexible hose 22 and is released only from the manifold 11 within the container 10.

As is mentioned above the object of the sterilization method and apparatus is to heat the refuse itself to a high enough temperature to sterilize the refuse. To monitor this condition, a wand 24 is inserted into the refuse, the wand 24 including a thermocouple whose leads pass through the cable 25.

In addition to the wand 24 for monitoring the interior of the refuse there is a pressure sensor 26 for monitoring the pressure within the autoclave. The autoclave 18 further includes pipes leading from the interior of the autoclave. These pipes are designated as 29 and 30, and will be discussed later.

Considering now the controls shown in FIG. 2, there is a steam supply feeding the pipe 32, the pipe 32 including an electrically controlled valve 34 and being connected to the steam inlet 21. A manual by-pass is provided at 35. Thus, so long as the valve 34 receives the appropriate signal, the valve 34 will be open, and steam will be admitted to the flexible hose 22 and to the manifold 11.

The signal to the valve 34 is controlled by the temperature controller 36 which receives information from the sensor 28. As a result, when the temperature within the autoclave 18 is below a predetermined value, the valve 34 will be open and steam will be admitted. When the sensor 28 indicates that the temperature has reached the predetermined value, the valve 34 will be closed.

It was mentioned above that the pressure within the autoclave 18 should remain relatively low. It has been found that a pressure of around 20 psi, or 14 kg/cm$^2$ is effective The pressure sensor 26 is connected to a controller 38 and to a valve 39, the valve 39 being in the line 29. As will be discussed later, when the sensor 26 indicates that the pressure within the autoclave is too high, the valve 39 will be opened to relieve the pressure. When the pressure is low enough, the valve 39 will be closed. Thus, as heated fluid continues to enter the autoclave 18, the valve 39 will be opened and closed to hold the pressure within the autoclave at the desired level.

In one successful embodiment of the present invention, the steam is introduced at about 100 psi (7 kg/cm$^2$), which means the steam has a temperature of about 328° F. (165° C.). It will therefore be understood that the refuse will be subjected to the high temperature steam during introduction of the steam for thorough heating of the refuse. Since the steam has a higher temperature than that to be achieved, and a higher pressure, the pressure must be monitored and controlled.

Once the desired temperature has been reached within the autoclave 18, the temperature is held for a predetermined length of time, the time at which the sterilization cycle has been completed. After the sterilization cycle, the pressure must be reduced, and the autoclave opened and the refuse container 10 removed. At the end of the sterilization cycle the valve 40 is opened to reduce the pressure within the autoclave. When the pressure is low enough, the door operator 41 will release the door so the autoclave 18 can be opened.

With the above description of the apparatus in mind, attention is directed to FIG. 3 of the drawings which is a flow chart showing the steps involved in sterilizing refuse in accordance with the present invention.

First, refuse is placed in the dumpster, or refuse container 10. It will be understood that the refuse is most often within a plurality of bags made of polyethylene or the like. In the prior art system, the pressure within the autoclave urges the bags together and insulates the center portion of the refuse. The result in the prior art is that the refuse is not raised to the desired temperature. The container 10 of the present invention therefore includes the injection manifold so that all steam entering the autoclave 18 first enters the container 10, and passes through the refuse in order to enter the autoclave 18.

Thus, after the refuse is in the container, the container is placed into the autoclave 18, and the wand 24 containing a temperature sensor is inserted into the refuse. The steam line, flexible hose 22, is connected to the container 10, and the autoclave is closed and sealed.

Steam is now injected directly into the refuse to heat the refuse itself; and, steam (or other heated fluid) continues to pass through the refuse until the autoclave reaches the desired temperature.

While steam is being injected, the pressure is monitored. It has been found that a relatively low pressure yields superior results. Of course the pressure must be high enough to achieve the required temperature at the particular geographical elevation, but extremely high pressure is undesirable. It has been found that a pressure around 20 psi, or 1.4 kg/cm$^2$ provides good results. Thus, while steam is being injected, there is an inquiry as to whether the pressure is greater than 19 psi (1.3 kg/cm$^2$). If the answer is No, monitoring simply continues; but, if the answer is Yes, the vent 29 is opened to relieve the pressure. Once the vent 29 is opened, there is a query as to whether the pressure is less than 19 (1.3). If No, the vent remains open; if Yes, the vent is closed.

While the pressure is being monitored, the temperature is also being monitored. Since the requirement for sterilizing international refuse is to hold the temperature at 212° F. (100° C.), the system of the present invention has taken a slightly higher temperature as the limit, simply to have a margin of safety. As temperature is monitored, there is the query, Is the temperature less than 215° F. (102° C.). So long as the answer is Yes, steam continues to be injected. When the answer is No, the steam inlet is stopped by closing valve 34, and a timer is started. There is then the question if the time equals 0.5 hour. So long as the answer is No, the process continues; and, when the answer is Yes, the timer is reset, steam is cut off, and the vent is opened.

It should be mentioned that, while the timer is running, the autoclave 18 must remain at 215° F. (102° C.); therefore, the temperature is still being monitored, and steam will be injected as before if the temperature falls below the selected temperature.

It will therefore be seen that the present invention provides a simple and effective means for sterilizing refuse. Pressure is provided so steam can be used at a high temperature, but the steam passes directly through the refuse to prevent the refuse itself from insulating parts of the refuse from the heat. The pressure is kept relatively low to reduce the dense packing of refuse, but high enough to achieve the desired temperatures.

The monitoring of temperatures and pressures can very easily be done manually, or by electronic computers or the like. Either will be quite simple to accomplish.

It will therefore be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

We claim:

1. A method for sterilizing refuse contained in a plurality of impervious bags, comprising the steps of enclosing said plurality of bags of refuse within a refuse container having a bottom, and placing said refuse container into a sealed container, said sealed container having an initial temperature and pressure substanstantially at ambient temperature and pressure, injecting heated fluid directly into said refuse container within said sealed container for raising said temperature and pressure within said sealed container, wherein said step of injecting heated fluid comprises releasing said heated fluid at a plurality of points distributed around said bottom of said refuse container for passing said heated fluid between and around said plurality of bags of refuse for heating said refuse during said step of injecting heated fluid directly into said refuse container within said sealed container, and further comprising the step of limiting the pressure within said sealed container during said step of injecting heated fluid directly into said refuse container within said sealed container.

2. A method as claimed in claim 1, wherein said step of limiting the pressure comprises the step of venting said sealed container when said sealed container has a pressure above a predetermined pressure of about 20 psig.

3. A method as claimed in claim 1, and further comprising the step of controlling the temperature within said sealed container during said step of injecting heated fluid directly into said refuse container within said sealed container.

4. A method as claimed in claim 3, wherein said step of controlling the temperature within said sealed container comprises the step of interrupting said step of injecting heated fluid directly into said refuse container within said sealed container.

5. A method as claimed in claim 4, and further comprising the step of starting a timer when the temperature within the sealed container reaches a predetermined temperature, and continuing said step of controlling the temperature until the timer reaches a predetermined length of time.

6. A method as claimed in claim 5 wherein said predetermined temperature is at least 212° F. or 100° C.

7. A method as claimed in claim 6 wherein said predetermined length of time is 0.5 hour.

* * * * *